(12) United States Patent
Baigar et al.

(10) Patent No.: US 9,816,914 B2
(45) Date of Patent: Nov. 14, 2017

(54) FLOW CELL

(71) Applicant: DIONEX SOFTRON GMBH, Germering (DE)

(72) Inventors: Erik Baigar, Munich (DE); Christian Andreas Hilmer, Germering (DE)

(73) Assignee: DIONEX SOFTRON GMBH, Germering (DE)

( * ) Notice: Subject to any disclaimer, the term of this patent is extended or adjusted under 35 U.S.C. 154(b) by 0 days.

(21) Appl. No.: 14/200,378

(22) Filed: Mar. 7, 2014

(65) Prior Publication Data
US 2014/0266266 A1 Sep. 18, 2014

(30) Foreign Application Priority Data

Mar. 12, 2013 (DE) .................. 10 2013 102 438

(51) Int. Cl.
| | | |
|---|---|---|
| G01F 1/84 | (2006.01) | |
| G01N 1/10 | (2006.01) | |
| G01N 21/01 | (2006.01) | |
| G01N 21/05 | (2006.01) | |
| G01N 21/41 | (2006.01) | |
| G01N 21/53 | (2006.01) | |
| G01N 21/59 | (2006.01) | |
| G01N 21/64 | (2006.01) | |
| G01N 21/65 | (2006.01) | |
| G01N 27/08 | (2006.01) | |

(Continued)

(52) U.S. Cl.
CPC ............. *G01N 21/01* (2013.01); *G01N 21/05* (2013.01); *G01N 21/41* (2013.01); *G01N 21/53* (2013.01); *G01N 21/59* (2013.01); *G01N 21/64* (2013.01); *G01N 21/65* (2013.01); *G01N 27/08* (2013.01); *G01N 30/74* (2013.01); *G01N 2021/0378* (2013.01); *G01N 2030/746* (2013.01); *Y10T 29/49826* (2015.01)

(58) Field of Classification Search
CPC ........ G01N 21/01; G01N 21/64; G01N 27/08; G01N 21/41; G01N 21/65; G01N 21/59; G01N 21/53; G01N 21/05; G01N 2030/746; G01N 2021/0378; G01N 30/74; Y10T 29/49826
USPC ...................... 324/693; 356/246; 73/861.355
See application file for complete search history.

(56) References Cited

U.S. PATENT DOCUMENTS 3,332,316 A 7/1967 Saunders
3,547,162 A 12/1970 Jacques
(Continued)

FOREIGN PATENT DOCUMENTS

CN 201000423 Y 1/2008
CN 201464357 U 5/2010
(Continued)

OTHER PUBLICATIONS

Barka et al., "Wege zur Miniaturisierung von Analysensystemen," Tiel 3: Automatische probeninjektion, LaborPraxis, Nov. 1997.
(Continued)

*Primary Examiner* — Farhana Hoque

(57) ABSTRACT

The invention relates to a flow cell for absorption detection, in which a tube through which flow is to pass is held at its opposite ends in a supporting flange in each case and is suspended in a substantially cantilevered manner, the two supporting flanges being connected rigidly to each other in order to avoid stresses accidentally introduced into the tube.

19 Claims, 3 Drawing Sheets

(51) Int. Cl.
*G01N 30/74* (2006.01)
*G01N 21/03* (2006.01)

(56) References Cited

U.S. PATENT DOCUMENTS

| | | | |
|---|---|---|---|
| 3,552,864 A | 1/1971 | Shields | |
| 4,076,420 A | 2/1978 | De Maeyer et al. | |
| 4,178,057 A | 12/1979 | McCormick | |
| 4,178,067 A | 12/1979 | Johnson et al. | |
| 4,198,081 A | 4/1980 | Harrison et al. | |
| 4,575,424 A | 3/1986 | Allington et al. | |
| 4,580,901 A | 4/1986 | Goldsmith | |
| 4,588,893 A | 5/1986 | Vidrine et al. | |
| 4,747,687 A | 5/1988 | Hoppe et al. | |
| 4,886,356 A | 12/1989 | Paradis | |
| 5,003,174 A | 3/1991 | Datwyler et al. | |
| 5,097,211 A * | 3/1992 | Schonstedt | G01V 3/15 |
| | | | 324/253 |
| 5,124,130 A * | 6/1992 | Costello | G01N 21/7703 |
| | | | 356/402 |
| 5,139,333 A | 8/1992 | Reinhard | |
| 5,140,169 A * | 8/1992 | Evens | G01N 21/05 |
| | | | 250/227.11 |
| 5,217,808 A | 6/1993 | Cobb | |
| 5,240,537 A | 8/1993 | Bodicky | |
| 5,259,112 A | 11/1993 | Matte et al. | |
| 5,417,925 A | 5/1995 | Goodale et al. | |
| 5,422,971 A * | 6/1995 | Honjo | G02B 6/3861 |
| | | | 385/139 |
| 5,650,846 A | 7/1997 | Yin et al. | |
| 5,692,088 A | 11/1997 | Ishiharada et al. | |
| 5,814,742 A | 9/1998 | Vissers et al. | |
| 5,905,271 A | 5/1999 | Wynn | |
| 6,122,049 A | 9/2000 | Sugiyama et al. | |
| 6,188,813 B1 | 2/2001 | Dourdeville et al. | |
| 6,200,531 B1 | 3/2001 | Liljestrand et al. | |
| 6,315,958 B1 | 11/2001 | Singh-Gasson et al. | |
| 6,444,175 B1 | 9/2002 | Singh-Gasson et al. | |
| 6,484,569 B1 | 11/2002 | Plant et al. | |
| 6,526,188 B2 | 2/2003 | Dourdeville et al. | |
| 6,587,195 B1 | 7/2003 | Jennings | |
| 6,747,740 B1 | 6/2004 | Leveille et al. | |
| 6,867,857 B2 | 3/2005 | Hobbs | |
| 7,184,141 B2 | 2/2007 | Brewer et al. | |
| 7,948,621 B2 | 5/2011 | Burns et al. | |
| 9,581,468 B2 | 2/2017 | Nguyen | |
| 9,585,781 B2 | 3/2017 | Fischell et al. | |
| 2002/0038998 A1 | 4/2002 | Fujita et al. | |
| 2003/0118485 A1 | 6/2003 | Singh-Gasson et al. | |
| 2004/0027568 A1 | 2/2004 | Maiefski et al. | |
| 2004/0036987 A1 | 2/2004 | Wisecarver et al. | |
| 2004/0066509 A1 | 4/2004 | Canty et al. | |
| 2004/0080744 A1 | 4/2004 | Hobbs | |
| 2005/0104607 A1* | 5/2005 | Byington et al. | 324/693 |
| 2005/0213088 A1 | 9/2005 | Brewer et al. | |
| 2007/0041009 A1* | 2/2007 | Iwano et al. | 356/246 |
| 2007/0064226 A1 | 3/2007 | Kolp et al. | |
| 2007/0077546 A1 | 4/2007 | Ji et al. | |
| 2008/0113447 A1 | 5/2008 | Krager et al. | |
| 2008/0231042 A1 | 9/2008 | Brayman et al. | |
| 2008/0236720 A1 | 10/2008 | Sigler et al. | |
| 2009/0033022 A1 | 2/2009 | Iki et al. | |
| 2009/0321356 A1 | 12/2009 | Gerhardt et al. | |
| 2010/0037706 A1* | 2/2010 | Sparks | G01F 1/8409 |
| | | | 73/861.355 |
| 2010/0118298 A1 | 5/2010 | Bair et al. | |
| 2011/0180211 A1 | 7/2011 | Jurischka et al. | |
| 2011/0194887 A1 | 8/2011 | Mankame et al. | |
| 2011/0299067 A1 | 12/2011 | Yokoyama et al. | |
| 2013/0242296 A1* | 9/2013 | Kenyon | G01N 15/1459 |
| | | | 356/243.2 |
| 2014/0266266 A1 | 9/2014 | Baigar et al. | |
| 2016/0327194 A1 | 11/2016 | Wells | |
| 2017/0016541 A1 | 1/2017 | Pears et al. | |

FOREIGN PATENT DOCUMENTS

| | | |
|---|---|---|
| CN | 201765178 U | 3/2011 |
| DE | 3603905 A1 | 8/1986 |
| DE | 3605518 A1 | 8/1987 |
| DE | 102007048738 | 4/2009 |
| DE | 102008027026 A1 | 12/2009 |
| EP | 0847767 B1 | 2/2005 |
| EP | 0956634 B1 | 10/2005 |
| JP | 4873193 | 10/1973 |
| JP | 59180448 | 10/1984 |
| JP | 60148956 | 10/1985 |
| JP | 02042337 | 2/1990 |
| JP | 02134563 | 5/1990 |
| JP | 05187995 | 7/1993 |
| JP | 8500188 | 1/1996 |
| JP | 9178648 | 7/1997 |
| JP | 2007047176 | 2/2007 |
| JP | 2011007758 | 1/2011 |
| WO | 2005015162 A2 | 2/2005 |
| WO | 2007009493 A1 | 1/2007 |
| WO | 2011079058 A1 | 6/2011 |
| WO | 2013113402 A1 | 8/2013 |

OTHER PUBLICATIONS

Dionex Corporation, PDA-100 (USB) Photodiode Array Detector Operator's Manual, Revision 03, Mar. 2006, 132 pages.
Dionex Corporation, UVD 170U and UVD 340U UV/VIS Detectors Operating Instructions, Revision 1.0-a, Jul. 2003, 54 pages.
Van Der Vlis, "Development of a needle device for on-line electroextraction-liquid chromatography," J. Chromatogr. A, 741, 13-21, 1996.
Vissers et al., "A fully automated microautosampler for micro and capillary liquid chromatography," International Laboratory, Jan. 1996.

* cited by examiner

FLOW CELL

CROSS REFERENCE TO RELATED APPLICATIONS

This application is claims the priority benefit under 35 U.S.C. §119 to German Patent Application No. 10 2013 102 438.6, filed on Mar. 12, 2013, entitled "Flow cell" the disclosure of which is incorporated herein by reference.

FIELD OF THE INVENTION

The present invention relates to a flow cell for optical detection, such as is used in the area of HPLC (high-performance liquid chromatography).

BACKGROUND

By means of such detectors, for example, the variation over time of the transmission of an eluting liquid is determined in order to obtain a chromatogram. The eluting liquid (below: sample) is led through the flow cell and irradiated with suitable light longitudinally or transversely with respect to the flow direction. In the case of absorption measurement, depending on the characteristics of the sample, the light is absorbed by the sample with different intensity at different wavelengths, so that only the non-absorbed proportion enters an optical conductor at the end of the flow cell and is fed to a suitable evaluation unit for further analysis.

The flow channel of the flow cell, through which the sample and the light are led, is usually formed as a thin tube. The light led along the tube is reflected on the tube inner side or—in the case of a transparent material of the tube wall—also on the outer side of the tube and thrown back into the interior of the tube. If, over a certain part of the distance between light inlet and light outlet, the light is propagated in the wall of the tube and not in the absorbing sample, systematic measurement errors occur, in particular in the case of highly absorbing samples. The wall thickness of the tube is preferably therefore chosen to be small, in particular in relation to the diameter of the fluid channel, but this makes the tube particularly sensitive to mechanical stress. In order to avoid any disruption to the reflection behavior on the outer tube wall, it is also necessary to prevent the contact of other substances with the outer side of the tube. Such a thin tube must be handled with great care in order to avoid damage during mounting and when mounted.

SUMMARY

The invention is based on the object of devising a unit for using a flow cell of the aforementioned type in which the tube is protected against external influences and is designed for the connection of at least one optical conductor and at least one sample feed. In addition, according to the invention a method for producing such a unit is to be provided.

The invention is based on the idea of securing the tube that is sensitive to external influences by means of a protective body surrounding said tube and at the same time to arrange said tube in a cantilevered manner within the protective pipe, that is to say supported only at its end. Furthermore, connections to the tube for the fluid to be examined and an optical conductor can be provided upstream and, respectively, downstream of the tube. For this purpose, the tube is respectively fitted to a supporting flange in its two end regions, the supporting flanges being connected rigidly to each other, which is preferably done by means of the protective pipe.

The flow cell according to the invention, together with positioning and/or connecting means, can form a measuring cell. The sample liquid to be examined can flow through the flow cell along a fluid channel formed as a tube. In order to analyze the sample, its absorption behavior with respect to light can be measured, for which purpose light can be introduced at one end of the tube. This is preferably done by means of an optical conductor arranged centrally in relation to the internal diameter of the tube, while the sample to be examined is able to flow into the tube through the annular gap between optical conductor and tube inner wall. At the other end of the tube, the non-absorbed light enters an optical conductor again, in order to be evaluated by using a unit connected downstream. This optical conductor is preferably also arranged centrally in relation to the tube internal diameter, so that the sample leaves the tube again through an annular gap. Other optical detection methods can likewise be used with the flow cell according to the invention.

According to the invention, the flow cell further comprises a protective pipe. The latter surrounds the tube along the longitudinal extent thereof, the tube being arranged in a cantilevered manner within the protective pipe. As a result, unintentional mechanical influence (stresses, impacts) on the tube from outside is prevented. In addition, the undesired action of dust or other deposits or contaminations on the tube outer side, which impair the reflection of light on the tube outer side, is avoided, According to an advantageous embodiment, the tube is held at its opposite ends in a supporting flange in each case, the two supporting flanges being connected rigidly to each other in order to avoid stresses accidentally introduced into the tube. The two flanges connected to each other form a supporting structure for the tube and, together with the protective pipe, prevent the introduction of undesired mechanical stresses into the tube. This makes it easier to handle the tube, which can then be gripped and positioned via the flange structure. As a result of holding the tube exclusively in its two end regions ("cantilevered"), it is further ensured that the reflection behavior of the tube outer wall is not impaired in the range important for the detection. In addition, the supporting flanges serve as connecting elements for the sample and/or the optical conductor.

The rigid connection of the two supporting flanges is expediently implemented by the protective pipe surrounding the tube. The protective pipe is closed off on both sides by the supporting flanges. In the interior thereof, the tube held by the supporting flanges preferably runs concentrically with respect to the protective pipe, a volume in the form of an annular gap being enclosed between protective pipe and tube. The protective pipe sealed off with two flanges forms a particularly rigid and therefore secure structure to receive the tube.

Various embodiments are suitable to form the protective pipe with supporting flanges. Protective pipe and supporting flanges can be separate elements, which have to be connected to each other in a suitable way in order to protect the tube. Latching or screw connections are suitable for this purpose. Particularly preferable are sealing connections by means of adhesive or plastic, which, for example, can harden. For instance, a UV-hardening plastic can be applied to a connecting region between supporting flange and protective pipe which, following appropriate positioning of supporting flange and protective pipe in relation to another, is hardened and therefore forms a rigid and preferably also tight connection.

Also conceivable is a single-piece design of at least one supporting flange and the protective pipe, for example in the form of a drilled or bored-out solid cylinder. The end of such a cylinder is given a preferably central cut-out, through which the tube can be inserted into the cylinder functioning as protective pipe. The internal diameter of the cylinder or of the bore is expediently chosen to be so large that contact between tube and cylinder is reliably avoided, in order to suspend the tube in a cantilevered manner. Also suitable as a protective pipe is a pipe with an internal diameter that is substantially constant over its entire length; the end regions would have to be considered as abnormal supporting flanges. By means of a fixing means (for example hardening plastic) applied to the end regions of such a pipe, the tube can be positioned and fixed within the protective pipe. The activation of the fixing means, by means of which the fixing action thereof is to be achieved, can be carried out in particular by means of a thermal process.

According to a further advantageous embodiment of the invention, the supporting flanges apply a predefinable tensile or compressive stress to the tube located between them, in the longitudinal direction of the latter. Such an introduced pre-stress is used to compensate for temperature-induced and/or pressure-reduced contraction or expansion behaviors of the tube in interaction with the rigid outer structure comprising supporting flanges and protective pipe. If the tube is, for example, fixed between the flanges with a low tensile stress, then when a warm fluid flows through the tube, the resultant longitudinal expansion of the tube will not lead to the latter giving way laterally or bending out. If protective pipe and tube have a different thermal expansion behavior, the previously introduced stresses in the tube are particularly well able to take account of these circumstances.

According to a further embodiment of the invention, the hollow space between protective pipe and tube is accessible through an opening in at least one supporting flange. Said hollow space can then be flushed or filled with an insert gas, which can also be used to avoid condensation on the tube outer side. The opening can also be used to introduce a highly thermally conductive medium between tube and protective pipe, in order in this way to reduce cell expansion stresses between protective pipe and tube.

Furthermore, the protective pipe itself can also have an access opening in order to reach into the interior. This can be a suitable, preferably closeable opening along the circumferential surface of the protective pipe. Alternatively, the protective pipe could also be formed in many parts, in order to obtain access to the interior of the protective pipe by means of partially breaking it down. In addition, by means of a detachable connection between the flanges and the protective pipe, the latter could be opened.

The fixing of the tube to the supporting flanges is expediently carried out by means of a fixing means, for example in the manner of a ferrule. This should permit a tight seal between tube and supporting flange and provide the tube with form-fitting and/or integral retention on the flange. Suitable fixing means are, in particular, a thermoplastic material and here, because of the good chemical properties, a representative from the polyether ketones (in particular PEEK, PEKEK, OXPEKK and the like). In order to avoid local stresses, the connection between tube and supporting flange is expediently made such that the fixing means is the single binding element between supporting flange and tube and, at the same time, ensures a minimum radial spacing between these two elements. For this purpose, the supporting flange can have a preferably centrally provided cut-out, through which the tube projects when fixed (and, after fabrication has been completed, ends flush with the outer side of the flange). The cut-out forms an annular gap between tube outer wall and supporting flange and can also have conical sections in the axial direction. The fixing means is introduced into the annular gap and produces a good connection between flange and tube. The fixing action between flange and tube is achieved by activating the fixing means. This is to be understood to include, in particular, the hardening thereof, a change in volume or development of adhesive forces, for example triggered by a thermal process. In addition, different thermal expansion coefficients of the two components to be connected can be used for the fixing.

On its side facing away from the tube, according to a further advantageous embodiment of the invention, the hardening fixing means forms a contact face for a sealing element. The sealing element is used for the secure connection of the sample feed, which is implemented by means of a connecting piece, which is arranged on the outer side of the supporting flange. In principle, the entire outer face of the supporting flange is suitable as a sealing face for the aforementioned connecting piece ("outer side" means a side facing away from the tube, substantially perpendicular to the tube axis). Following the insertion of the tube into the supporting flange and the fixing of said tube there, the outer side of the supporting flange can be ground in a suitable way in order to form a smooth sealing face, in the centre of which the fixing means machined at the same time and the tube enclosed by the fixing means are positioned.

Depending on the sample characteristics, it may be necessary to avoid contact of the sample with the material of the supporting flange. To this end, the aforesaid sealing element must rest on the sealing face in the region of the ferrule, so that a sample fluid flowing through the sealing element (for example an O-ring or flat seal) can if need be come into contact with the chemically neutral or resistant fixing means (PEEK or the like).

For the arrangement of the connecting piece, via which the sample is fed in and also the optical conductor is inserted into the tube, according to a further advantageous embodiment of the invention, provision is made for at least one supporting flange to have positioning means, in order to be able to align the connecting piece with the relevant supporting flange. The positioning means can be formed in one piece and/or detachably with the supporting flange and preferably has a rotationally symmetrical shape, which can also have lugs and/or cut-outs for defined rotational positioning of the connecting piece to be inserted.

According to one embodiment, the positioning means are fixed to the outer side of the supporting flange by means of a suitable substance. The substance can achieve its fixing action, for example, by means of hardening or adhesive forces exerted by the substance, for example triggered by a thermal process. In this way, the exact arrangement of the connecting piece can be ensured even for the case in which the supporting flange and/or the position of the tube held by the latter deviates from a position that is to be expected, for example because of dimensional or joining tolerances. The positioning means can in particular have the form of a pot with a preferably central hole, the pot resting with its underside on the outer side of the supporting flange or on the sealing face of the latter. The central hole is used to lead the optical conductor and the sample through and should be arranged concentrically with respect to the opening of the tube such that, as the connecting piece is inserted into the positioning means, the optical conductor held by the connecting piece is aligned exactly concentrically with respect to the axis of the tube. The alignment and fixing of the positioning means with and to the supporting flange can be carried out manually, with the aid of mechanical means or else by using optical inspection means.

High optical requirements with regard to high transmission in the wavelength range of interest are placed on the material for the tube. Suitable, for example, are quartz, CaF, sapphire or $Al_2O_3$. These materials have a low thermal expansion coefficient, so that the tube can be inserted easily, in particular under a previously introduced tensile stress. For the protective pipe, any material is suitable which, if required, is suitable for the permanent maintenance of a tensile stress between the supporting flanges and for absorbing stresses applied externally (e.g. by the mounting of the entire unit in the device).

The method according to the invention for producing the above-described flow cell comprises at least the following steps:

a) positioning a fixing means in a cut-out in at least one supporting flange and positioning a tube in the fixing means;

b) hardening and/or deforming the fixing means, in particular by means of a thermal process, so that the tube is subsequently fixed to at least one supporting flange.

Following these method steps, the supporting flange could be arranged on a protective pipe surrounding the tube and be connected to the former. In principle, it would also be conceivable to produce the connection between supporting flange and protective pipe first, in order only then to fix the tube in the centre of the supporting flange. However, if the tube is not to be arranged without stress but with a pre-stress (tensile or compressive stress) between the flanges, then the fixing of the tube to the two flanges first is recommended, said flanges then being connected to the protective pipe whilst maintaining the desired pre-stress. Following hardening of the connection between the flanges and the protective pipe, the pre-stress is "frozen in" the tube as a result.

A subsequently conceivable method step provides for the formation of the sealing face on the outer side of at least one supporting flange, which is expediently done by grinding off using various, preferably decreasing, grain sizes. In order to avoid contamination of the tube in the process, the access openings of the latter can be closed temporarily, for example with a soluble varnish. In addition, an opening on the supporting flange that leads into the hollow space between tube and protective pipe can be closed in this way.

The flow cell according to the invention is suitable for carrying out the absorption detection but is likewise also suitable for other measuring methods. For example, a scattered light measurement could be carried out in the hollow space between tube and protective pipe. Light scattered into this hollow space from the interior of the tube is then used as a measure for the number/size of the scattering particles of the sample. If the protective pipe is transparent, the detection can also be carried out completely outside the protective pipe.

The flow cell is also suitable for fluorescence or Raman measurements. In this case, excitation light can be provided outside the circumferential surface of the tube. The light scattered or emitted by the sample is collected in the tube and led away for evaluation via an optical conductor at the end of the tube. Given a protective pipe that is transparent to the excitation light, this light can also be directed inward onto the tube from outside the protective pipe. In this case, the protective pipe can itself be formed as a spectral filter. However, the excitation light can also be introduced into the sample within the tube, while the light emitted by the sample is picked up by a suitable sensor on the tube outer side (inside or outside the protective pipe) or an optical conductor arranged there, and fed to the evaluation.

The flow cell according to the invention is likewise suitable for the determination of electrochemical properties of the sample, such as the electrical conductivity or dielectric constant of the latter. To this end, via the connecting pieces, suitable electrodes (e.g. made of platinum or titanium) can make contact with the fluid flowing through the tube. Alternatively, it would be conceivable to form the two supporting flanges as electrodes; these would have to be isolated electrically despite the rigid connection, but this could be implemented via an electrically non-conductive supporting pipe. Furthermore, in this embodiment, it would have to be ensured that the fluid enters into electrically conductive contact with the supporting flanges, so that the previously described O-ring must be chosen to be larger than the outer diameter of the hardened fixing means in the centre of the flange. An optical detection method could advantageously be carried out simultaneously with the measurement of the electrochemical properties. At the same time, the cantilevered tube is well insulated and has a low electrical capacitance. Sensitive detection of the electrochemical parameters is therefore to be expected.

If the outer space of the tube is occupied by another medium (solid or liquid), then the refractive index in the outer space and therefore the critical angle of the internal total reflection can be varied. Since the refraction of the measuring light during the transition from the feeding optical conductor into the fluid depends on the refractive index of the latter, the distribution of the acceptance angle of the light in the interior of the tube changes with the refractive index of the fluid. If the maximum occurring acceptance angle is greater than can be kept in the tube by internal total reflection at the tube outer side, then the transmitted quantity of light depends on the refractive index of the fluid and can be used as a measured variable for the purpose (refractive index measurement).

The refractive index at the tube outer side can also be defined by the tube being provided on its outer side with a specific coating or outer skin which exhibits the desired refractive behavior.

A particularly expedient embodiment of the invention provides for the interspace between protective pipe and tube to be pressurized, so that the compressive strength of the tube itself is increased. Since the tube merely has to withstand the differential pressure with respect to the surroundings, the increase in this surrounding pressure also leads to an increase in the possible internal pressure in the tube. In addition, by means of a positive pressure, long-term protection of the tube can be ensured, for example with respect to condensation of moisture, contamination and the formation of a coating by particles or as a result of UV-triggered reaction of gases or direct absorption of light in the evanescent wave by gases.

BRIEF DESCRIPTION OF THE DRAWINGS

The invention is to be explained in more detail below by using figures.

DETAILED DESCRIPTION OF EMBODIMENTS

Figure 1:
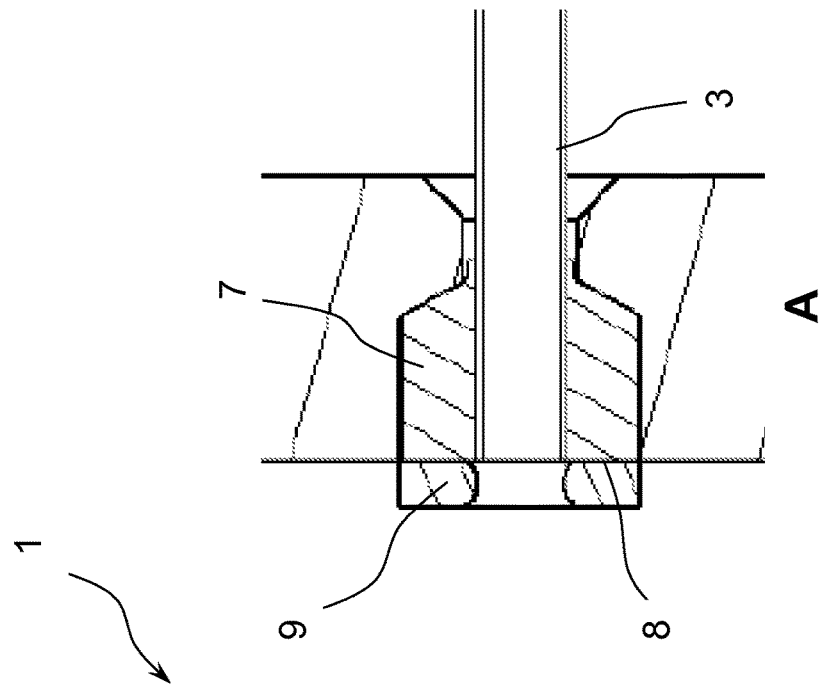
FIG. 1 shows a schematic sectional illustration of part of a flow cell with an enlarged detail view.
Figure 1:
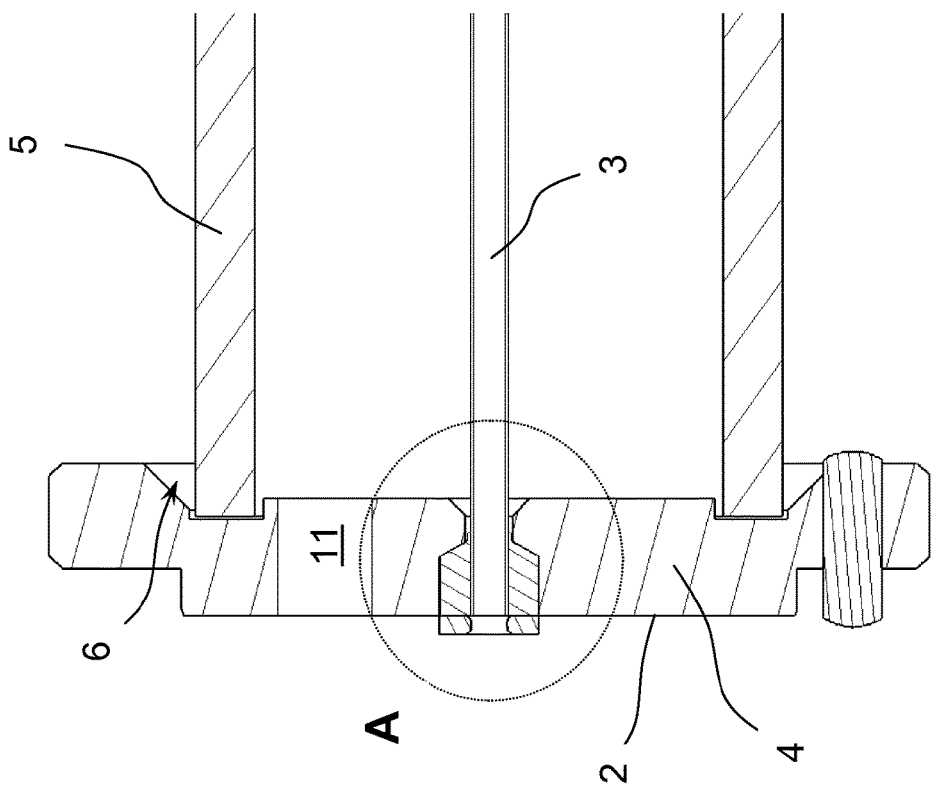

In FIG. 1, the section through the left-hand section of a flow cell 1 according to the invention is illustrated in a schematic partial view, the right-hand section being designed symmetrically with respect thereto. A protective pipe 5 is covered with a supporting flange 4 at the left-hand free end thereof. Protective pipe 5 and supporting flange 4 are firmly connected to each other with a UV-hardening plastic 6. Arranged in the interior of the protective pipe 5 is a tube 3, which extends concentrically with respect to the axis of the protective pipe over its entire length and in each case ends flush with the outer side 2 of the flange 4. A sample to be examined is intended to be led through the tube 3 and exposed to the action of light in the axial direction in the process.

The connection of the sample feed and of the optical channel on the outer side 2 of the flange 4 is not illustrated. It is made via a connection piece which, in the centre of the supporting flange 4, is arranged on the outer side 2 of the latter, exact positioning of the connecting piece relative to the opening of the tube 3 being important.

The supporting flange 4 has an opening 11, via which the interspace between the outer circumferential surface of the tube 3 and the inner side of the protective pipe 5 is accessible, for example in order to feed in inert gas.

Leading through and fixing the tube 3 is provided in the centre of the supporting flange 4, as shown by the enlarged extract in the right-hand part of FIG. 1. Here, in a cut-out in the supporting flange, which tapers conically toward the tube 3 following a cylindrical region, a hardened fixing means 7 is introduced as ferrule. Via the fixing means 7, the tube 3 is fixed to the supporting flange 4. This ensures that the tube 3 does not touch the supporting flange 4 itself but, as it is led through the supporting flange 4, is held exclusively by the ferrule.

The outer side 2 of the supporting flange 4 has been machined to form a sealing face, the section in the centre of the supporting flange 4, formed by the fixing means 7, continuing the sealing face and running flush with the outer side 2 as a contact face 8. The contact face 8 is used for the arrangement of an O-ring 9, which is pressed against the supporting face 8 via the connecting piece, not shown. As a result of the seal in the region of the contact face 8 formed by the fixing means 7, it is ensured that the sample fluid flowing into or out of the tube 3 from the left in FIG. 1 does not come into contact with the material of the supporting flange 4.

Figure 2:
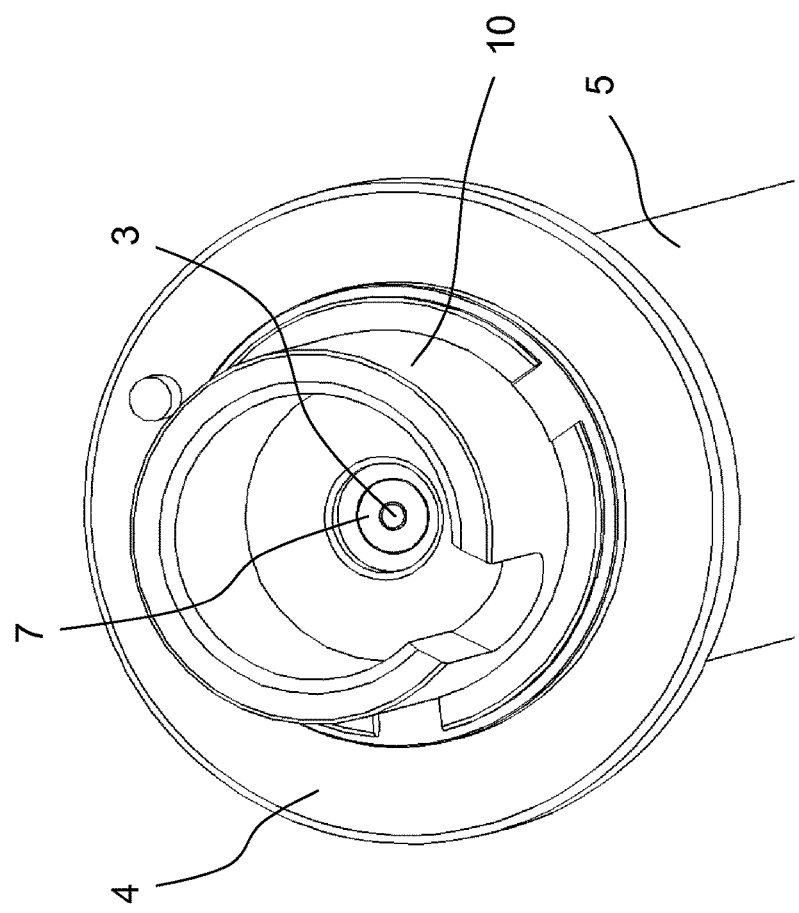
FIGS. 2 and 3 show embodiments of positioning means.

FIG. 2 shows, in a simplified perspective view, a substantially annular body 10 which is arranged on the supporting flange 4 and which serves as a positioning means for the connecting piece. The positioning means comprises a tube section which, at one end, has a covering plate with a central opening. The opening of the tube 3 and the contact face 8 of the fixing means 7 are accessible through the opening. Given previously performed alignment and fixing of the positioning means 10, a connecting piece formed to be complementary thereto is positioned with its foremost section concentric with respect to the tube 3 as it is inserted, so that the optical conductor held by the connecting piece is able to project into the interior of the tube 3 by a predefined amount. On the outer side of the optical conductor, and sealed off with respect to the outside by the O-ring 9, not shown in FIG. 2, the sample material to be examined passes into the tube 3 and out again at the opposite end of the latter.

Figure 3:
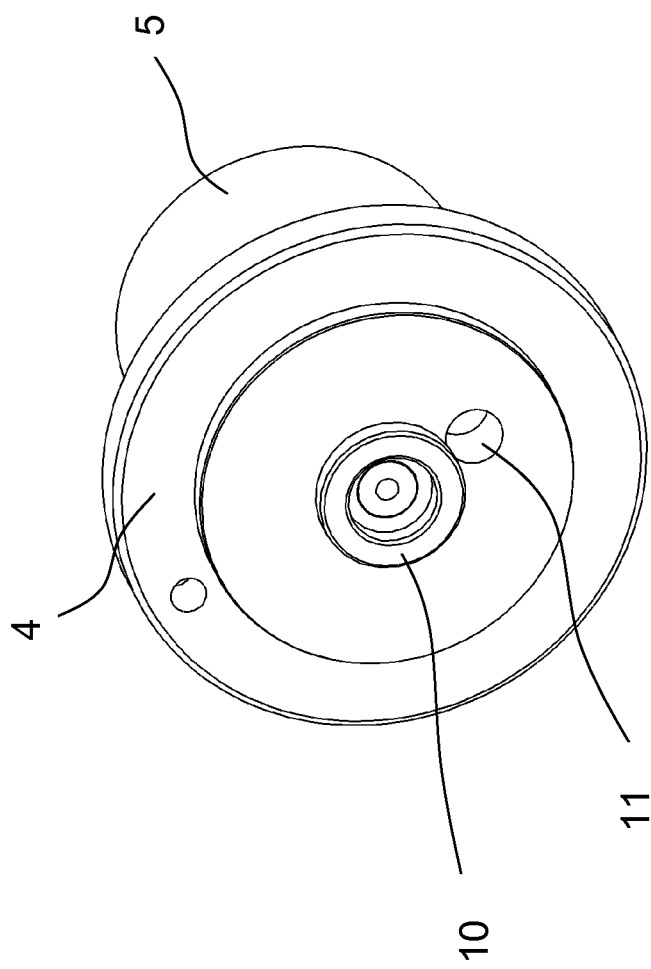

A somewhat different embodiment of a positioning means 10 is shown by FIG. 3. This positioning means is of a lower axial length and also has a smaller diameter as compared with the variant according to FIG. 2. Here, too, a connecting piece that is designed to be complementary thereto is again aligned exactly as it is inserted into the positioning means. The smaller radial dimension of the positioning means according to FIG. 3 permits simpler access to the opening 11 in the supporting flange 4 in order to reach the interior of the protective pipe 5.

LIST OF REFERENCE SYMBOLS

1 Flow cell
2 Outer side
3 Tube
4 Supporting flange
5 Protective pipe
6 UV-hardening plastic
7 Fixing means
8 Contact face
9 O-ring
10 Positioning means
11 Opening

What is claimed is:
1. A flow cell for optical detection comprising:
   a) a tube that includes a fluid channel, in which the tube is configured to flow a sample liquid along the fluid channel,
   b) in which the flow cell is configured to conduct a light through the fluid channel transversely or longitudinally,
   c) a protective pipe, in which the tube is surrounded in a longitudinal direction by the protective pipe and is arranged in a cantilevered manner within the protective pipe, in which an interspace is between the protective pipe and the tube, and an interspace extends the entire length of the protective pipe, whereby deposition or contact with an outer side of the tube is avoided, and
   d) two supporting flanges, in that opposite ends of the tube are held by the two supporting flanges, the two supporting flanges are rigidly connected to the protective pipe,
   in that at least one of the two supporting flanges has a cut-out where the tube projects into the cut-out when fixed.

2. The flow cell according to claim 1, in that the two supporting flanges are connected to the protective pipe by a connecting material.

3. The flow cell according to claim 2, in that the connecting material is an adhesively bonded UV-hardening plastic.

4. The flow cell according to claim 1, in that at least one of the two supporting flanges is an end of the protective pipe formed in one piece therewith, which surrounds the tube.

5. The flow cell according to claim 1, in that the two supporting flanges apply a predefinable tensile or a compressive stress to the tube located between the two supporting flanges, in the longitudinal direction.

6. The flow cell according to claim 1, in that the tube is connected to the two supporting flanges via a fixing means.

7. The flow cell according to claim 6, in that the cut-out is a central cut-out for the fixing means.

8. The flow cell according to claim 7, in that the tube is spaced apart from the two supporting flanges in a radial direction by the fixing means.

9. The flow cell according to claim 7, in that, on an outer side of the at least one of the two supporting flanges facing away from the tube, the fixing means has a contact face for a sealing element.

10. The flow cell according to claim 1, in that at least one of the two supporting flanges has a positioning device, where the at least one supporting flange and the positioning device are formed as one piece, the positioning device is configured to align therewith a connecting piece where the connecting piece provides the sample liquid and the light.

11. The flow cell according to claim 1, in that at least one of the two supporting flanges has a positioning device, where the positioning device is detachably fixed to the at least one supporting flange, the positioning device is configured to align therewith a connecting piece where the connecting piece provides the sample liquid and the light.

12. The flow cell according to claim 1, in that at least one of the two supporting flanges has an opening, the opening configured to receive an inert gas applied to the interspace between the outer side of the tube and an inner side of the protective pipe.

13. The flow cell according to claim 1, in that the interspace includes an annular gap.

14. A method to produce a flow cell, the flow cell comprising:
   a) a tube that includes a fluid channel, in which the tube is configured to flow a sample liquid along the fluid channel,
   b) in which the flow cell is configured to conduct a light through the fluid channel transversely or longitudinally,
   c) a protective pipe, in which the tube is surrounded in a longitudinal direction by the protective pipe and is arranged in a cantilevered manner within the protective pipe, in which an interspace is between the protective pipe and the tube, and the interspace extends the entire length of the protective tube, whereby deposition or contact with an outer side of the tube is avoided, and
   d) two supporting flanges, in that opposite ends of the tube are held by the two supporting flanges, the two supporting flanges are rigidly connected to the protective pipe,
   in that the tube is connected to the two supporting flanges via a fixing means,
   in that at least one of the two supporting flanges has a central cut-out for the fixing means where the tube projects into the cut-out when fixed, the method comprising:
   a) positioning the fixing means in the central cut-out in the at least one of the two supporting flanges and positioning the tube in the fixing means; and
   b) activating the fixing means to fix the tube to the at least one supporting flange.

15. The method according to claim 14, in that the at least one of the two supporting flanges is positioned on the protective pipe surrounding the tube to connect the at least one supporting flange to the protective pipe by a connecting material.

16. The method according to claim 14 further comprising:
   following the fixing of the tube, grinding an outer side of the at least one of the two supporting flanges together with the fixing means and the tube to form a sealing face.

17. The method according to claim 14, in that the at least one supporting flange has a positioning device, the positioning device is configured to align therewith a connecting piece where the connecting piece provides the sample liquid and the light, the method further comprising:
   positioning the positioning device on the at least one supporting flange by one of a tactile means, a mechanical aid, or an optical aid; and
   fixing the positioning device to the at least one supporting flange.

18. A method of using a flow cell for an optical detection, the flow cell comprising:
   a) a tube that includes a fluid channel, in which the tube is configured to flow a sample liquid along the fluid channel,
   b) in which the flow cell is configured to conduct a light through the fluid channel transversely or longitudinally,
   c) a protective pipe, in which the tube is surrounded in a longitudinal direction by the protective pipe and is arranged in a cantilevered manner within the protective pipe, in which an interspace is between the protective pipe and the tube, and an interspace extends the entire length of the protective pipe, whereby deposition or contact with an outer side of the tube is avoided, and
   d) two supporting flanges, in that opposite ends of the tube are held by the two supporting flanges, the two supporting flanges are rigidly connected to the protective pipe,
   in that at least one of the two supporting flanges has a cut-out where the tube projects into the cut-out when fixed, the method comprising:
   detecting the sample liquid with the optical detection selected from the group consisting of an absorption detection, a scattered light measurement, a fluorescence measurement, a Raman measurement, and a refractive index measurement.

19. A method of using a flow cell, the flow cell comprising:
   a) a tube that includes a fluid channel, in which the tube is configured to flow a sample liquid along the fluid channel,
   b) in which the flow cell is configured to conduct a light through the fluid channel transversely or longitudinally,
   c) a protective pipe, in which the tube is surrounded in a longitudinal direction by the protective pipe and is arranged in a cantilevered manner within the protective pipe, in which an interspace is between the protective pipe and the tube, and an interspace extends the entire length of the protective pipe, whereby deposition or contact with an outer side of the tube is avoided, and
   d) two supporting flanges, in that opposite ends of the tube are held by the two supporting flanges, the two supporting flanges are rigidly connected to the protective pipe, in that at least one of the two supporting flanges has a cut-out where the tube projects into the cut-out when fixed, the method comprising:
   measuring electrochemical properties of the sample liquid, in which the electrochemical properties is selected from the group consisting of an electrical conductivity and a dielectric constant of the sample liquid.

* * * * *